United States Patent [19]

Valyocsik

[11] Patent Number: 5,441,721
[45] Date of Patent: Aug. 15, 1995

[54] SYNTHESIS OF POROUS CRYSTALLINE MCM-58

[75] Inventor: Ernest W. Valyocsik, Yardley, Pa.

[73] Assignee: Mobil Oil Corp., Fairfax, Va.

[21] Appl. No.: 347,919

[22] Filed: Dec. 1, 1994

Related U.S. Application Data

[63] Continuation-in-part of Ser. No. 205,437, Mar. 4, 1994, which is a continuation-in-part of Ser. No. 137,705, Oct. 18, 1993, abandoned.

[51] Int. Cl.[6] .............................................. C01B 39/04
[52] U.S. Cl. ................................... 423/706; 423/709; 423/718; 502/62
[58] Field of Search ............... 423/702, 705, 709, 718, 423/706; 502/62, 65, 66, 73, 74

[56] References Cited

U.S. PATENT DOCUMENTS

| | | | |
|---|---|---|---|
| 3,702,886 | 11/1972 | Argauer et al. | 423/705 |
| 3,709,979 | 1/1973 | Chu | 423/700 |
| 3,832,449 | 8/1974 | Rosinski et al. | 423/705 |
| 3,972,983 | 8/1967 | Ciric | 423/705 |
| 4,016,245 | 4/1977 | Plank et al. | 423/708 |
| 4,076,842 | 2/1978 | Plank et al. | 423/704 |
| 4,592,902 | 6/1986 | Valyocsik | 423/706 |
| 4,698,217 | 10/1987 | Valyocsik | 423/706 |
| 4,954,325 | 9/1990 | Rubin et al. | 423/706 |
| 4,981,663 | 1/1991 | Rubin | 423/706 |
| 5,200,377 | 4/1993 | Zones et al. | 502/62 |
| 5,268,161 | 12/1993 | Nakauawa | 423/706 |
| 5,340,563 | 8/1994 | Zones et al. | 423/706 |

Primary Examiner—Mark L. Bell
Assistant Examiner—David R. Sample
Attorney, Agent, or Firm—Alexander J. McKillop; Dennis P. Santini

[57] ABSTRACT

This invention relates to a new method for synthesis of porous crystalline material designated MCM-58. The crystalline MCM-58 product of the present method exhibits a distinctive X-ray diffraction pattern.

17 Claims, 1 Drawing Sheet

Degrees two-theta

SYNTHESIS OF POROUS CRYSTALLINE MCM-58

CROSS-REFERENCE TO RELATED APPLICATION

This is a continuation-in-part of application Ser. No. 08/205,437, filed Mar. 4, 1994, which is a continuation-in-part of application Ser. No. 08/137,705, filed Oct. 18, 1993, now abandoned.

BACKGROUND OF THE INVENTION

1. Field of the Invention

This invention relates to synthesis of the novel composition of synthetic porous crystalline material designated MCM-58.

2. Description of the Prior Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, for example an alkali metal or an alkaline earth metal cation. This can be expressed wherein the ratio of the Group IIIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449), zeolite ZSM-20 (U.S. Pat. No. 3,972,983); ZSM-35 (U.S. Pat. No. 4,016,245); zeolite ZSM-23 (U.S. Pat. No. 4,076,842); zeolite MCM-22 (U.S. Pat. No. 4,954,325); and zeolite MCM-35 (U.S. Pat. No. 4,981,663), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicate of varying alumina and metal content.

SUMMARY OF THE INVENTION

The present invention is directed to a method for synthesis of a novel composition of a porous crystalline material, named MCM-58. The calcined form of the porous crystalline material synthesized by this invention possesses a very high acid activity and exhibits a high sorption capacity. MCM-58 is reproducibly synthesized by the present method in high purity.

DESCRIPTION OF SPECIFIC EMBODIMENTS

Figure 1:
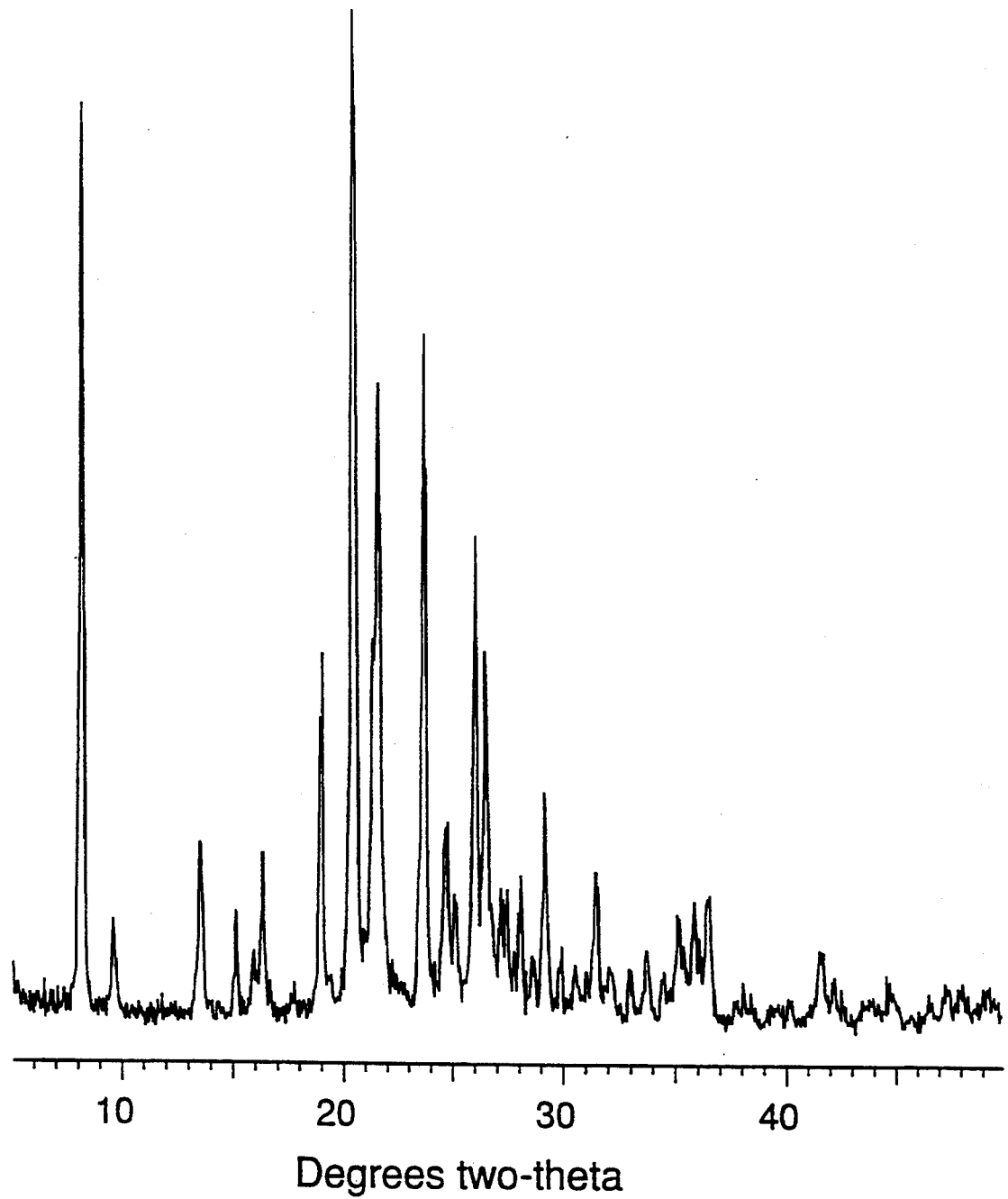
FIG. 1 shows the X-ray diffraction pattern of the as-synthesized product of Example 4, hereinafter presented.

The crystalline MCM-58 material synthesized by the method of this invention has a composition involving the molar relationship:

$$X_2O_3:(n)YO_2$$

wherein X is a trivalent element, such as aluminum, boron, iron, indium, and/or gallium, preferably aluminum; Y is a tetravalent element such as silicon, tin, and/or germanium, preferably silicon; and n is from greater than about 10 to about 1000, usually from greater than about 10 to about 400, more usually from about 20 to about 200. In the as-synthesized form, the material has a formula, on an anhydrous basis and in terms of moles of oxides per n moles of $YO_2$, as follows:

$$(0.1-2)M_2O:(0.2-2)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

MCM-58 synthesized hereby is thermally stable and in the calcined form exhibits significant hydrocarbon sorption capacity. To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-58 material synthesized hereby appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 10.89 ± 0.30 | s-vs |
| 9.19 ± 0.30 | vw |
| 6.55 ± 0.29 | vw-w |
| 5.86 ± 0.28 | vw-w |
| 5.57 ± 0.27 | vw-w |
| 5.43 ± 0.26 | vw-w |
| 4.68 ± 0.25 | vw-m |
| 4.36 ± 0.25 | w-vs |
| 4.17 ± 0.23 | vw-m |
| 4.12 ± 0.23 | vw-s |
| 3.78 ± 0.20 | wv-s |
| 3.61 ± 0.15 | vw-w |
| 3.54 ± 0.15 | vw |
| 3.44 ± 0.15 | vw-m |
| 3.37 ± 0.15 | vw-m |
| 3.06 ± 0.15 | vw-w |
| 2.84 ± 0.15 | vw |
| 2.72 ± 0.13 | vw |
| 2.66 ± 0.12 | vw |
| 2.46 ± 0.12 | vw |
| 2.17 ± 0.10 | vw |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

When used as a catalyst, MCM-58 may be subjected to treatment to remove part or all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline MCM-58 material can be transformed by thermal treatment. This thermal treatment is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

The crystalline material synthesized by the present invention, when employed either as an adsorbent or as a catalyst in an organic compound conversion process should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the MCM-58 in a vacuum, but a longer time is required to obtain a sufficient amount of dehydration.

The method of this invention for synthesizing crystalline MCM-58 material exhibiting a characteristic X-ray diffraction pattern including d-spacing maxima values shown in Table I comprises preparing a mixture capable of forming said material, said mixture comprising sources of potassium or mixture of potassium and another alkali or alkaline earth metal (M), e.g. potassium alone or with sodium, an oxide of trivalent element (X), e.g. aluminum, gallium, boron and/or iron, an oxide of tetravalent element (Y), e.g. silicon and/or germanium, water, and directing agent: (R) comprising benzyltropanium cations, said reaction mixture having a composition, in terms of mole ratios of oxides, within the following ranges:

| Reactants | Useful | Preferred |
|---|---|---|
| $YO_2/X_2O_3$ | 15 to 60 | 20 to 40 |
| $H_2O/YO_2$ | 5 to 200 | 20 to 100 |
| $OH^-/YO_2$ | 0 to 3 | 0.10 to 0.50 |
| $M/YO_2$ | 0 to 3 | 0.10 to 2 |
| $R/YO_2$ | 0.02 to 1.0 | 0.10 to 0.50 |

In the present synthesis method, the preferred source of $YO_2$ comprises predominately solid $YO_2$, for example at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) is preferred for MCM-58 formation from the above mixture. Preferably, therefore, the $YO_2$, e.g., silica, source contains at least about 30 wt. % solid $YO_2$, e.g., silica, and more preferably at least about 40 wt. % solid $YO_2$, e.g., silica.

The organic directing agent R for use herein is the cation benzyltropanium, having a formula $C_{15}H_{22}N^+$, and may be represented as follows:

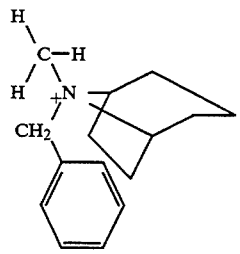

The source of this organic cation may be, for example, the halide, e.g., chloride or bromide, or hydroxide salt. The source of organic directing agent used in the following examples was synthesized by reacting benzylbromide with tropane as follows.

A 37.6 gram (0.3 mole) quantity of tropane was dissolved in 300 ml of absolute ethanol, then transferred to a 2-liter 3-necked reaction flask equipped with a stirrer, a thermometer, a condenser, and surrounded by a heating mantle. Now 60 grams (excess) of benzylbromide was weighed out and transferred to the 2-liter reaction flask with an additional 300 ml of absolute ethanol.

The reaction flask was then sealed and the heater was turned on. The reaction mixture was heated overnight at the temperature of the refluxing ethanol solvent before termination of the synthesis by quenching the reaction flask to $-40°$ C. in a dry ice/acetone bath after addition of anhydrous diethyl ether to the reaction mixture.

Copious quantities of white crystalline benzyltropanium bromide product had separated from the ethanol solvent. The crystalline product was filtered while cold on a Buechner funnel. The crystalline product was then washed with anhydrous diethyl ether, then dried in an air stream overnight on the filtering funnel. The actual yield of benzyltropanium bromide product for this synthesis was 88.9 grams (95.8% theoretical).

Crystallization of the MCM-58 crystalline material can be accomplished by the present method at either static or stirred conditions in a suitable reactor vessel, such as for example, polypropylene jars or teflon lined or stainless steel autoclaves. The total useful range of temperatures for crystallization is from about 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of the new crystals may be facilitated by the presence of at least 0.01 percent, preferably 0.10 percent and still more preferably 1 percent, seed crystals (based on total weight) of crystalline product.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material product of this invention can be used to catalyze a wide variety of chemical conversion processes including many of present commercial/industrial importance. Examples of chemical conversion processes which are effectively catalyzed by the crystalline material of this invention, by itself or in combination with one or more other catalytically active substances including other crystalline catalysts, include those requiring a catalyst with acid activity. Specific examples include:

(1) toluene disproportionation, with reaction conditions including a temperature of from about 200° C. to about 760° C., a pressure of from about atmospheric to about 60 atmospheres, a weight hourly space velocity (WHSV) of from about 0.1 $hr^{-1}$ to about 20 $hr^{-1}$, and a hydrogen/hydrocarbon mole ratio of from 0 (no added hydrogen) to about 50, to provide disproportionation product, including p-xylene;

(2) transalkylation of aromatics, in gas or liquid phase, with reaction conditions including a temperature of from about 100° C. to about 500° C., a pressure of from about 1 to about 200 atmospheres, and a WHSV of from 1 $hr^{-1}$ to about 10,000 $hr^{-1}$;

(3) reaction of paraffins with aromatics to form alkylaromatics and light gases with reaction conditions including a temperature of from about 260° C. to about 375° C., a pressure of from about 0 to about 1000 psig, a WHSV of from about 0.5 $hr^{-1}$ to about 10 $hr^{-1}$, and a hydrogen/hydrocarbon mole ratio of from 0 (no added hydrogen) to about 10;

(4) paraffin isomerization to provide branched paraffins with reaction conditions including a temperature of from about 200° C. to about 315° C., a pressure of from about 100 to 1000 psig, a WHSV of from about 0.5 $hr^{-1}$ to about 10 $hr^{-1}$, and a hydrogen/hydrocarbon mole ratio of from about 0.5 to about 10; and (5) alkylation of aromatics with olefins with reaction conditions including a temperature of from about 200° C. to about 500° C., a pressure of from about 0 to 500 psig, a total WHSV of from about 0.5 $hr^{-1}$ to about 50 $hr^{-1}$, a hydrogen/hydrocarbon mole ratio of from 0 (no added hydrogen) to about 10, and an aromatic/olefin mole ratio of from 1 to about 50.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, such as silica, zirconia, titania, magnesia, beryllia, alumina, and mixtures thereof.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for 2,2-dimethylbutane (2,2-DMB) and n-hexane, they were Equilibrium Adsorption values determined as follows.

A weighed sample of the calcined adsorbent was contacted with the desired pure adsorbate vapor in an adsorption chamber, evacuated to less than 1 mm and contacted with 40 Torr of n-hexane or 2,2-DMB vapor, pressures less than the vapor-liquid equilibrium pressure of the respective adsorbate at 30° C. for n-hexane and 90° C. for 2,2-DMB. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in mg/g of calcined adsorbant.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

EXAMPLES 1-6

Experiments were conducted for synthesis of crystalline product MCM-58 by the method of this invention. In these experiments, $Al_2(SO_4)_3 \cdot 18H_2O$ and KOH pellets for potassium or NaOH for sodium were dissolved in deionized water. The benzyltropanium bromide prepared above was then dissolved in the solution. Colloidal silica sol (30 wt. % $SiO_2$) was then mixed into the solution. The mixture was stirred for 2 minutes to produce a uniform, fluid hydrogel, having, respectively, the compositions shown in Table II where R is the cation of benzyltropanium bromide.

The hydrogel of each experiment was then transferred to a 300 ml stainless steel autoclave equipped with a stirrer. The autoclave was capped and sealed; and 400 psig of inert gas was introduced into the autoclave. Stirring and heating were started immediately. Crystallizations were carried out at 170° C. with stirring.

Crystalline products were recovered, filtered, washed with deionized water, and dried on a filter funnel in an air stream under an infrared lamp. The dried crystalline powder products were then submitted for X-ray diffraction and chemical analysis.

TABLE II

| | Mixture Composition (mole ratios)* | | | | |
|---|---|---|---|---|---|
| Example | $SiO_2/Al_2O_3$ | $K^+/SiO_2$ | $Na^+/SiO_2$ | Reaction time, days | Products |
| 1 | 15 | — | 0.44 | 7 | Mordenite |
| 2 | 25 | 0.62 | — | 7 | MCM-58 + trace mordenite |
| 3 | 30 | — | 0.37 | 7 | Mordenite |
| 4 | 30 | 0.57 | — | 7 | MCM-58 |
| 5 | 30 | 0.57 | — | 7 | MCM-58 |
| 6 | 30 | 0.57 | — | 7 | MCM-58 |

*$H_2O/SiO_2 = 40$, $OH^-/SiO_2 = 0.30$, $R/SiO_2 = 0.20$

The X-ray diffraction pattern generated by the product of Example 4 is presented in FIG. 1.

Chemical analysis results for the as-synthesized products of Example 4 is presented in Table III.

TABLE III

| | | Moles per Mole $Al_2O_3$ | | | Composition$^{(1)}$ | | |
|---|---|---|---|---|---|---|---|
| Example | Moles C/Mole N | $N_2O$ | $K_2O$ | $SiO_2$ | Al/100 Td | $K^+$/100 Td | $R^{(2)}$/100 Td |
| 6 | 15.6 | 0.93 | 1.5 | 26.3 | 7.1 | 10 | 6.5 |

$^{(1)}$Calculated on the basis of $100(SiO_2 + AlO_2)$ tetrahedra
$^{(2)}$R = benzyltropanium cation There appears to be no clear trend in the alkali metal content per 100 tetrahedra, but there does appear to be approximately 6 template cations per 100 tetrahedra in the MCM-58 framework, indicating templating activity for the benzyltropanium cation.

EXAMPLES 7-9

MCM-58 products of Examples 4, 5, and 6 were weighed into quartz boats, then placed into a Heviduty ® tube furnace and sealed with nitrogen gas flowing through the furnace tube. The heating of the furnace was begun at 2° C./minute from room temperature to 538° C. When the furnace reached the maximum temperature, the flowing gas was switched to air, and the calcination of the zeolite was continued for 15 hours before termination.

The air calcined samples were ammonium exchanged with 1 M $NH_4NO_3$ at 80° C. for 6 hours. After ammonium exchange, the zeolites were filtered, washed with deionized water, and dried in an air stream on the filter funnel under an infrared heat lamp.

The calcination procedure was repeated on the ammonium-exchanged materials in the tube furnace in the same manner as described above, except this time the samples were held at 538° C. for 8 hours to convert them to HMCM-58. Examples 7, 8, and 9 products were MCM-58 materials from the products of Examples 4, 5, and 6, respectively.

Constraint Index

A convenient measure of the extent to which a crystalline material provides control to molecules of varying sizes to its internal structure is the Constraint Index (CI) of the material. Zeolites which provide a highly restricted access to and egress from their internal structures have a high value for the Constraint Index, and zeolites of this kind usually have pores of small size, e.g., less than 5 Angstroms. On the other hand, zeolites which provide relatively free access to their internal structures have a low value for the Constraint Index and usually have pores of large size, e.g., greater than 8 Angstroms. The method by which Constraint Index is determined is described fully in U.S. Pat. No. 4,016,218, incorporated herein by reference for details of the method.

Constraint Index values for some typical zeolites are as follows:

|  | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 0.6–1.5 (399° C.–454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

EXAMPLE 10

The Constraint Index of HMCM-58 was determined to be 0.3 at 316° C. This value falls within the classification of the more open structures having 12-membered rings. Hence, it is concluded from the catalytic Constraint Index Test result that HMCM-58 contains at least a 12-membered ring structure.

What is claimed is:

1. A method for synthesizing crystalline material exhibiting a characteristic X-ray diffraction pattern including d-spacing maxima values shown in Table I which comprises (i) preparing a mixture capable of forming said material, said mixture comprising sources of potassium or potassium and alkali or alkaline earth metal (M), an oxide of trivalent element (X), an oxide of tetravalent element (Y), water, and directing agent (R) comprising benzyltropanium cations, and having a composition, in terms of mole ratios, within the following ranges:

| $YO_2/X_2O_3$ | 15 to 60 |
|---|---|
| $H_2O/YO_2$ | 5 to 200 |
| $OH^-/YO_2$ | 0 to 3 |
| $M/YO_2$ | 0 to 3 |
| $R/YO_2$ | 0.02 to 1.0, |

(ii) maintaining said mixture under sufficient conditions including a temperature of from about 80° C. to about 250° C. until crystals of said material are formed; and (iii) recovering said crystalline material from step (ii).

2. The method of claim 1 wherein said mixture has the following composition ranges:

| $YO_2/X_2O_3$ | 20 to 40 |
|---|---|
| $H_2O/YO_2$ | 20 to 100 |
| $OH^-/YO_2$ | 0.10 to 0.50 |
| $M/YO_2$ | 0.10 to 2 |
| $R/YO_2$ | 0.10 to 0.50. |

3. The method of claim 1 wherein said mixture further comprises seed crystals in sufficient amount to enhance synthesis of said crystalline material.

4. The method of claim 1 wherein said X comprises aluminum, boron, iron, gallium, indium, or a mixture thereof; and said Y comprises silicon, germanium, tin, or a mixture thereof.

5. The method of claim 1 wherein X comprises aluminum and Y comprises silicon.

6. The method of claim 1 comprising replacing ions of the crystalline material recovered in step (iii), at least in part, by ion exchange with an ion or a mixture of ions selected from the group consisting of hydrogen and hydrogen precursors, rare earth metals, and metals from Groups IIA, IIIA, IVA, IB, IIB, IIIB, IVB, VIB, and VIII of the Periodic Table of Elements.

7. The method of claim 6 wherein said replacing ion is hydrogen or a hydrogen precursor.

8. The recovered crystalline material of claim 1.

9. A synthetic porous crystalline material characterized by an X-ray diffraction pattern including values substantially as set forth in Table I of the specification and having a composition, on an anhydrous basis and in terms of moles of oxides per n moles of $YO_2$, expressed by the formula:

$$(0.1-2)M_2O:(0.2-2)R:X_2O_3:nYO_2$$

wherein M is potassium or potassium and alkali or alkaline earth metal and R comprises a benzyltropanium cation.

10. The crystalline material of claim 9 wherein n is from greater than about 10 to about 400.

11. The crystalline material of claim 9 wherein n is from about 20 to about 200.

12. The crystalline material of claim 9 wherein X is a trivalent element selected from the group consisting of boron, iron, indium, gallium, aluminum, and a combination thereof; and Y is a tetravalent element selected from the group consisting of silicon, tin, germanium, and a combination thereof.

13. The crystalline material of claim 9 wherein X comprises aluminum, boron, or a combination thereof and Y comprises silicon.

14. The crystalline material of claim 9 wherein X comprises aluminum and Y comprises silicon.

15. A composition comprising the crystalline material of claim 9 and a matrix.

16. The composition of claim 15 wherein said matrix comprises alumina, silica, zirconia, titania, magnesia, beryllia or a combination thereof.

17. A mixture capable of forming crystalline material exhibiting a characteristic X-ray diffraction pattern including d-spacing maxima values shown in Table I upon crystallization, said mixture comprising sources of potassium or potassium and alkali or alkaline earth metal (M); trivalent element (X) oxide selected from the group consisting of oxide of aluminum, boron, iron, gallium, indium, and mixtures thereof; tetravalent element (Y) oxide selected from the group consisting of oxide of silicon, germanium, tin, and mixtures thereof; water; and directing agent (R) comprising benzyltropanium cations, and having a composition, in terms of mole ratios, within the following ranges:

| | |
|---|---|
| $YO_2/X_2O_3$ | 15 to 60 |
| $H_2O/YO_2$ | 5 to 200 |
| $OH^-/YO_2$ | 0 to 3 |
| $M/YO_2$ | 0 to 3 |
| $R/YO_2$ | 0.02 to 1.0. |

* * * * *